US010668299B2

United States Patent
Krechting et al.

(10) Patent No.: US 10,668,299 B2
(45) Date of Patent: Jun. 2, 2020

(54) BRACHYTHERAPY APPLICATORS HAVING ULTRASOUND ELEMENTS

(71) Applicant: Nucletron Operations B.V., Veenendaal (NL)

(72) Inventors: Paulus Cornelis Hendrikus Maria Krechting, Veenendaal (NL); Wilhelmus Petrus Martinus Maria Van Erp, Veenendaal (NL); Jan F. L. De Becker, Veenendaal (NL); Anton J. G. Welberg, Veenendaal (NL)

(73) Assignee: Nucletron Operations B.V., Veenendaal (NL)

( * ) Notice: Subject to any disclaimer, the term of this patent is extended or adjusted under 35 U.S.C. 154(b) by 295 days.

(21) Appl. No.: 15/564,960

(22) PCT Filed: Apr. 11, 2016

(86) PCT No.: PCT/NL2016/050248
§ 371 (c)(1),
(2) Date: Oct. 6, 2017

(87) PCT Pub. No.: WO2016/163885
PCT Pub. Date: Oct. 13, 2016

(65) Prior Publication Data
US 2018/0071549 A1  Mar. 15, 2018

Related U.S. Application Data

(60) Provisional application No. 62/145,962, filed on Apr. 10, 2015.

(51) Int. Cl.
*A61N 5/10* (2006.01)
*A61B 8/08* (2006.01)
(Continued)

(52) U.S. Cl.
CPC ............ *A61N 5/1016* (2013.01); *A61B 8/085* (2013.01); *A61B 8/12* (2013.01); *A61B 8/4281* (2013.01);
(Continued)

(58) Field of Classification Search
CPC ......... A61B 8/085; A61B 8/12; A61B 8/4281; A61B 8/4477; A61B 2090/3784;
(Continued)

(56) References Cited

U.S. PATENT DOCUMENTS 4,794,931 A * 1/1989 Yock ................. A61B 8/12
600/439
2008/0097470 A1 4/2008 Gruber et al.
(Continued)

FOREIGN PATENT DOCUMENTS

| CN | 102348480 A | 2/2012 |
| WO | 2015023307 A1 | 2/2015 |
| WO | 2015039995 A1 | 3/2015 |

OTHER PUBLICATIONS

International Preliminary Report on Patentability dated Jul. 7, 2017, in corresponding Application No. PCT/NL2016/050248 (9 pages).

*Primary Examiner* — Christine H Matthews
*Assistant Examiner* — Joshua Daryl D Lannu
(74) *Attorney, Agent, or Firm* — Bookoff McAndrews, PLLC

(57) ABSTRACT

A brachytherapy system includes a brachytherapy applicator. The brachytherapy applicator includes an applicator tube and a radiation source configured to deliver radiation to a tumor. At least a portion of the applicator tube is configured to conform to at least a portion of a patient's anatomy. At least one ultrasound element or probe is coupled to or embedded with the applicator tube.

23 Claims, 5 Drawing Sheets

(51) Int. Cl.
*A61B 8/12* (2006.01)
*A61B 8/00* (2006.01)
*A61B 90/00* (2016.01)

(52) U.S. Cl.
CPC .......... *A61B 8/4477* (2013.01); *A61B 8/4488* (2013.01); *A61B 8/483* (2013.01); *A61N 5/1049* (2013.01); *A61B 2090/3784* (2016.02); *A61N 2005/1018* (2013.01); *A61N 2005/1058* (2013.01)

(58) Field of Classification Search
CPC .... A61B 8/483; A61B 8/4488; A61N 5/1016; A61N 5/1049; A61N 2005/1018; A61N 2005/1058
See application file for complete search history.

(56) References Cited

U.S. PATENT DOCUMENTS

| | | | |
|---|---|---|---|
| 2010/0069878 A1* | 3/2010 | Parsai | A61M 25/1002 604/500 |
| 2010/0145132 A1 | 6/2010 | Isham | |
| 2013/0109908 A1* | 5/2013 | Rahimian | A61N 5/1016 600/6 |
| 2013/0211176 A1 | 8/2013 | Habib | |
| 2013/0216114 A1* | 8/2013 | Courtney | A61B 5/0066 382/130 |
| 2014/0187960 A1* | 7/2014 | Corl | A61B 8/12 600/466 |

* cited by examiner

BRACHYTHERAPY APPLICATORS HAVING ULTRASOUND ELEMENTS

CROSS-REFERENCE TO RELATED APPLICATIONS

This application is the U.S. national phase entry under 35 U.S.C. § 371 of International Application No. PCT/NL2016/050248, filed on Apr. 11, 2016, which claims priority to U.S. provisional Patent Application No. 61/145,962, filed on Apr. 10, 2015, which is incorporated herein by reference in its entirety.

TECHNICAL FIELD

The present disclosure relates generally to applicators and, more particularly, to brachytherapy applicators containing ultrasound elements.

BACKGROUND

Brachytherapy is a type of radiation therapy that has proven efficacy for treating a variety of types of cancers, such as cervical cancer. In brachytherapy procedures, radiation is delivered to cancerous regions by positioning a radiation source in close proximity to a tumor, typically by using a physical applicator equipped with a radiation source. Brachytherapy procedures may offer advantages over external beam radiation therapies by enabling improved targeting of cancerous cells, thus reducing the likelihood that healthy cells are radiated during treatment.

Development of a conformal dose plan for cervical cancer patients receiving brachytherapy is typically guided by images obtained via one or more imaging modalities. For example, in some instances, two-dimensional (2D) X-ray imaging may be chosen for treatment planning due to its low cost and minimal impact on the workflow. However, since the information available through 2D X-ray imaging is inherently limited due to its 2D nature (e.g., it may be possible to visualize the applicator but not the patient's anatomy), many dose plans are based on one or more types of three-dimensional (3D) imaging modalities. For instance, magnetic resonance imaging (MRI) and computed tomography (CT) may be used to gain a greater depth of information than would be acquired with 2D X-ray imaging.

However, image-guided 3D conformal dose planning with MRI and/or CT introduces significant monetary costs, accessibility difficulties, and lengthened procedure times. For example, the imaging department in a hospital is typically located in a different area than the treatment department, thus requiring time and expenses associated with patient transport and facilities planning. In an attempt to overcome these difficulties, trans-abdominal ultrasound (TAUS) and trans-rectal ultrasound (TRUS) modalities have been developed. Unfortunately, TAUS does not enable visualization of the anatomy of interest since the rectum, bowel, applicator, and needles may not be visible in the acquired images. Similarly, TRUS may not enable visualization of the bladder, bowel, and applicator. Further, combining TAUS and TRUS presents alignment and calibration difficulties, in addition to introducing undesirable workflow complexity in the operating room. Additionally, air present in the field of view complicates the use of ultrasonic modalities.

Accordingly, there exists a need for improved imaging systems that enable image-guided brachytherapy treatment of cervical cancer while addressing one or more of these drawbacks.

SUMMARY

To overcome at least some of the problems mentioned here above, a brachytherapy system is provided, comprising: a brachytherapy applicator comprising an applicator body and a radiation source configured to deliver radiation to a tumor, wherein at least a portion of the applicator body is configured to conform to at least a portion of a patient's anatomy; and at least one ultrasound element, element array, or probe coupled to the applicator body. The ultrasound element is preferably provided on a wall shaped to the patients anatomy, to be in direct contact with the patients anatomy.

In accordance with one embodiment of the present disclosure, a brachytherapy system includes a brachytherapy applicator. The brachytherapy applicator includes an applicator tube and a radiation source configured to deliver radiation to a tumor. At least a portion of the applicator tube is configured to conform to at least a portion of a patient's anatomy. At least one ultrasound element or probe is coupled to the applicator tube.

In accordance with another embodiment of the present disclosure, a brachytherapy system includes a brachytherapy applicator having a body including at least one channel extending therethrough and being configured to deliver radiation to a tumor. The brachytherapy system also includes at least one ultrasound probe configured to be inserted into the at least one channel and moved along the length of the channel.

In accordance with another embodiment of the present disclosure, a brachytherapy system includes a brachytherapy applicator including an applicator tube and at least one ovoid coupled to the applicator tube and configured to conform to at least a portion of a patient's vagina. The brachytherapy system also includes at least one ultrasound probe disposed on or in an outer surface of the brachytherapy applicator.

BRIEF DESCRIPTION OF THE DRAWINGS

The accompanying drawings, which are incorporated in and constitute a part of this disclosure, illustrate several embodiments and aspects of the present disclosure, and together with the description, serve to explain certain principles of the presently disclosed embodiments.

DETAILED DESCRIPTION OF EXAMPLE EMBODIMENTS

Provided herein are embodiments of devices and systems that integrate an ultrasound (US) element, array of US elements, or US probe with a brachytherapy applicator to enable 3D conformal dose planning for cervical or other cancer patients at the point of care in the operating room. The disclosed embodiments may integrate the US element, element array, or probe with the brachytherapy applicator in a variety of ways described in more detail below. In some embodiments described below, an US element or US element array may include one or more crystals or other materials capable of generating and receiving US signals, and an US probe may include a device with such US elements that may be moved from one position to another during treatment. Further, it should be noted that the embodiments described below may be implemented separately or in any suitable combination, depending on implementation-specific considerations.

Figure 1:
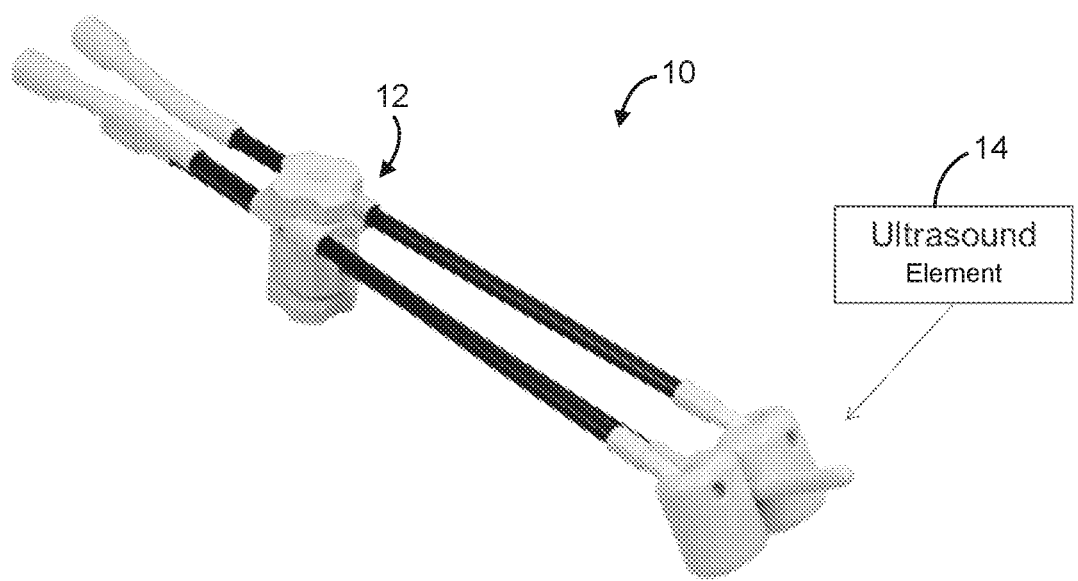
FIG. 1 illustrates a brachytherapy applicator and an ultrasound element, consistent with embodiments of the present disclosure.

Turning now to the drawings, FIG. 1 schematically illustrates a brachytherapy system 10 including a gynecologic brachytherapy applicator 12 and an US element 14. The illustrated brachytherapy applicator 12 is a standard applicator set having a fixed geometry and enabling conformal treatment planning with the use of transverse slices. However, the depiction of the standard applicator set in FIG. 1 is merely a non-limiting example, not meant to limit the scope of presently contemplated embodiments. Indeed, in other embodiments, the gynecological brachytherapy applicator 12 shown in FIG. 1 (or any applicators shown in other figures) may be any suitable gynecologic brachytherapy applicator, such as but not limited to vaginal multi-channel applicators, interstitial ring applicators, ring applicators, Fletcher Williamson applicator sets, Ti vaginal cylinder applicator sets, Miami vaginal applicator sets, shielded cylindrical applicator sets, combined interstitial and intracavitary applicator sets, ring-based applicator sets, and combinations thereof.

Further, although the illustrations described herein depict gynecological applicators, this type of applicator is merely an example not meant to limit the types of applicators encompassed by the presently contemplated embodiments. In some embodiments, the applicator 12 may not be a gynecological applicator. For example, the applicator 12 may be a device designed for applications related to esophageal, skin, rectal, prostate needles, lung, and other body site applications.

Suitable gynecological applicators for use as the applicator 12 may include tandem and ovoids, tandem and rings, and cylinders. The applicator 12 may include templates, such as prostate and/or gynecological templates. The applicator 12 may also include skin applicators, esophageal applicators, rectal applicators, lung applicators, nasopharynx applicators, breast and/or tongue applicators, breast, CT and/or MRI, conditional and/or safe applicators. In embodiments in which the applicator 12 includes a breast or tongue applicator, the US elements 14 may be positioned against the side of the plates towards the breast or tongue.

The US element 14 is schematically illustrated in FIG. 1 and may take on a variety of suitable forms, depending on implementation-specific considerations. For example, the US element 14 may be a 3D or moving 2D probe. Further, the US element 14 may include a phased array either with or without an associated multiplexer. In other embodiments, the US element 14 may include a rotating crystal either with or without a mirror.

The US element 14 and the gynecologic brachytherapy applicator 12 may be combined, coupled, or otherwise integrated together in a variety of suitable ways. For example, the US element 14 may be positioned in one or more channels of the applicator 12, attached to an outer surface of the applicator 12, or integrated in another manner with the applicator 12. FIGS. 2-7 show example embodiments for coupling and/or integrating the gynecologic brachytherapy applicator 12 with the US element 14.

During operation of the brachytherapy system 10, the brachytherapy applicator 12 is inserted into the patient, for example, by advancing the applicator 12 into a patient's vagina. The US element 14 may be used before, during, or after insertion into the patient to transmit acoustic signals into the patient and receive acoustic signals back from the patient after such signals have interacted with the patient's anatomy and the surrounding environment. The US element 14 may be inserted into the patient substantially concurrently with insertion of the applicator 12, or an US probe may be inserted into the patient after the applicator 12 is positioned. The US element 14 may both send and receive US signals.

Further, in some embodiments, the US element 14 may be positioned to contact the patient's tissue before insertion and may remain in contact with the patient's tissue during insertion. For example, in one embodiment, the US element 14 may include a plurality of US elements disposed in or on foam, which expands during insertion into the vagina and presses the US elements against the patient's vaginal wall. In this way, air in the patient's vagina may be reduced or eliminated and replaced by the foam. The foam may then function as a transmission medium for the ultrasound waves transmitted and received by the US element 14, thus rendering the area within the patient's vagina suitable for probing with ultrasonic modalities.

In some embodiments, the probe may be moved over a desired length or portion of the patient's anatomy to obtain a 3D image of the region of interest. The US element(s) 14 may be excited in a specific order to create an ultrasound wave that is able to cover the region of interest. As such, the brachytherapy applicator 12 shown in FIG. 1 may include US emitting and receiving elements, such as crystals, on the ovoid and/or at the intrauterine tube. In some embodiments, the conductive elements (which may be electrical or optical) may be integrated in the tubing wall. In a specific embodiment an applicator has an US receiving and emitting element designed with a center focus aimed at an organ at risk, organ of interest. For example, for a gynealogical applicator, organs of interest are known to the skilled person and may be the Bladder, Rectum and Sigmoid, at least one of these organs having a specific US element having a center focus aimed at the organ. See for further details FIG. 9. In an embodiment, the ultrasound element, has a field of view that in use, is directed at an organ of interest, in particular any of the bladder, sigmoid or rectum. Furthermore, preferably, the ultrasound element is provided on the wall shaped according to the patients anatomy, to be in direct contact with the patients tissue, for optimal imaging purposes. Based on the received acoustic signals, one or more images, either 2D or 3D, may be reconstructed.

During the acquisition of the ultrasound images, it may be desirable to reduce or eliminate air from the field of view. To that end, it may be desirable to surround the applicator 12 with a medium that reduces or prevents the likelihood that air will be present in the vagina. Therefore, in some embodiments, the vagina may be filled by packing with fabric soaked in a gel, filling with a compressible foam or other material, filling with gel, or filling with a compliant balloon full of a material substantially free of air or other undesirable gases.

Further, in certain embodiments, the environment in the area to be imaged (e.g., the distal 5 cm of the vagina) may be filled with a fluid or solid material. Suitable materials that could be used include but are not limited to a water-based foam that expands between the applicator 12 and the patient's tissue, a rigid gel compressed between the applicator 12 and the tissue, compliable balloon(s) filled with a material such as saline, fabric filled with a gel that may be pressed out of the fabric to form a uniform water-based matrix during packaging, a deformable sponge filled with a gel that is compressed in the free space, a water-based foam such as PUR foam, a two-component composite material that hardens (e.g., within about a minute) and includes water, a frozen water area, and so forth. Additionally, in one embodiment, the vagina may be filled with a plurality of water-filled particles, thus packing the applicator 12 in place. The particles may be formed from a rubber material having the air removed therefrom, resulting in a rigid, water-filled anatomical shaped system.

In some embodiments, the 3D data acquired via operation of the US element 14 may be utilized in 3D conformal dose planning for cervix treatments and may offer one of more advantages over conventional approaches making use of MRI or CT imaging modalities. For example, by using the ultrasound-based brachytherapy system 10, the total time for a cervical cancer treatment procedure may be reduced because the US element 14 may be used at the point of care in the operation room during the treatment procedure. Use of at least some of the presently disclosed embodiments may not require that the patient be relocated to an imaging department from the operation room to perform imaging.

Further, since the brachytherapy system 10 of FIG. 1 includes the US element 14 integrated with the applicator 12, and air has been reduced or eliminated from the field of view, the system 10 may enable visualization of the desired anatomy and features of the surrounding environment with a single device. For example, a single device may be utilized to visualize the applicator 12, the cervix, the parametrium, the uterus, and/or other anatomy of interest, without the need for more than one device (e.g., without the need for a TAUS device and/or a TRUS device).

Further, due to the integration of the US element 14 with the applicator 12, the image reconstruction of the applicator 12 may be improved as compared to traditional systems. Further, during the insertion of needles, the US element 14 may provide real time feedback on the needle position within the patient. Similarly, during treatment of the patient, the brachytherapy system 10 may provide real time feedback regarding the relative position between the tumor, the applicator 12, and/or one or more other portions of the patient's anatomy.

In some embodiments, the foregoing features of the brachytherapy system 10 may further enable creation of a conformal treatment plan for the imaged patient based on only ultrasound images, not MRI, CT, or X-ray images. Further, shifts of the applicator 12, or other changes that occur during treatment, may be detected in real time, thus enabling a clinician to dynamically adapt the current or subsequent treatment plan for the patient, or to readjust the position of the applicator 12, during the treatment procedure. For example, in one embodiment, a feedback loop may be employed to enable repositioning of the applicator 12 based on the determined position of the applicator 12 with respect to the tumor at various points during treatment.

Further, it should be noted that in some embodiments, the brachytherapy system 10 may be used for quality assurance purposes. In such embodiments, imaging with the US element 14 may occur during treatment to verify whether the conditions under which the treatment plan is made remain the same during treatment. For example, the brachytherapy system 10 may be used to determine if there is movement of the applicator 12 in relation to the tumor or critical organs, which may result in an under or over dosage of the tumor, thus increasing the likelihood of treatment side effects.

Figure 2:
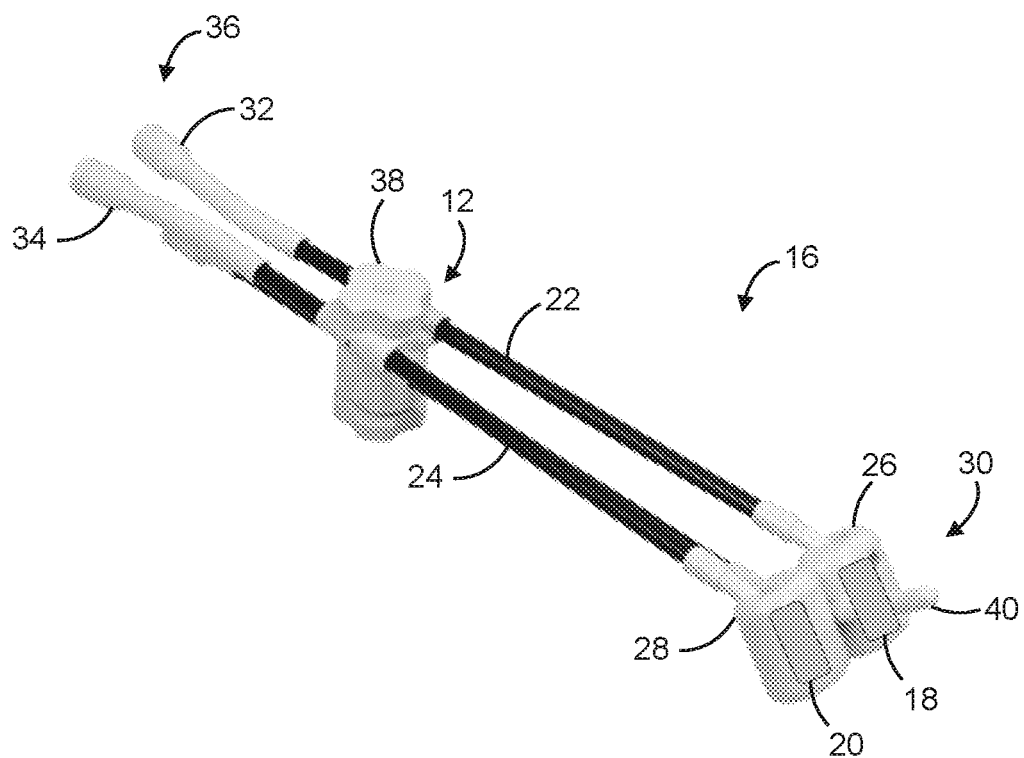
FIG. 2 illustrates a brachytherapy applicator having one or more ultrasound elements located thereon, consistent with embodiments of the present disclosure.

FIG. 2 illustrates a brachytherapy system 16 including the brachytherapy applicator 12 and US sensors 18 and 20. In this embodiment, the brachytherapy applicator 12 is a standard applicator set including two applicator tubes 22 and 24 having ovoids 26 and 28 at a distal end 30 and ports 32 and 34 at a proximal end 36. A tube clamp 38 is disposed about the applicator tubes 22 and 24 to hold the assembly together. The applicator tubes 22 and 24 may have one or more closed tube end extensions 40 configured to hold one or more radiation sources for treatment. Further, each applicator tube 22 and 24 may have an inner channel that enables a source to move through the tubes 22 and 24. For example, a radiation source, a dummy source, or a tracking device may move through the channels.

The ovoids 26 and 28 may be various shapes and sizes to provide effective treatment to a patient. In one embodiment, the shape of the ovoids 26 and 28 may be matched to the anatomical structure of the patient, increasing or decreasing in size to fit the patient. The ovoids 26 and 28 may include shielding, which may attenuate or direct the radiation that may emanate from sources placed at the end of applicator tubes 22 and 24. Further, the ovoids 26 and 28 may include apertures for the placement of interstitial needles.

In the illustrated embodiment, the US sensors 18 and 20 are located on the ovoids 26 and 28, respectively. The US sensors 18 and 20 may be located in any desirable location about the ovoids 26 and 28, such as on the top and bottom of the ovoids 26 and 28, or on the intrauterine tube. Further, the US sensors 18 and 20 may be attached to the ovoids 26 and 28 in any suitable manner, for example, by using biocompatible adhesives or tethering mechanisms, snap fit, screws, bayonet connection, friction fit, and so forth.

The applicator tubes 22 and 24 may be secured using one or more of the tube clamps 38. In some embodiments, the tube clamp 38 may prevent the sliding or rotation of applicator tubes 22 and 24 with respect to one another. For example, the tube clamp 38 may include a fastener, screw, or other securement mechanism to apply a force to a side of the applicator tubes 22 and 24.

The applicator tubes 22 and 24 may also include the ports 32 and 34 that may each receive devices, such as radiation sources, dummy sources, or tracking devices. The ports 32 and 34 may be covered, for example, with port caps, before, during, or after use. During use, an automated process may be employed. Once a needle is properly positioned within the patient, an actuator may be connected, and the radiation source is then inserted through the ports 32 and 34.

Figure 3:
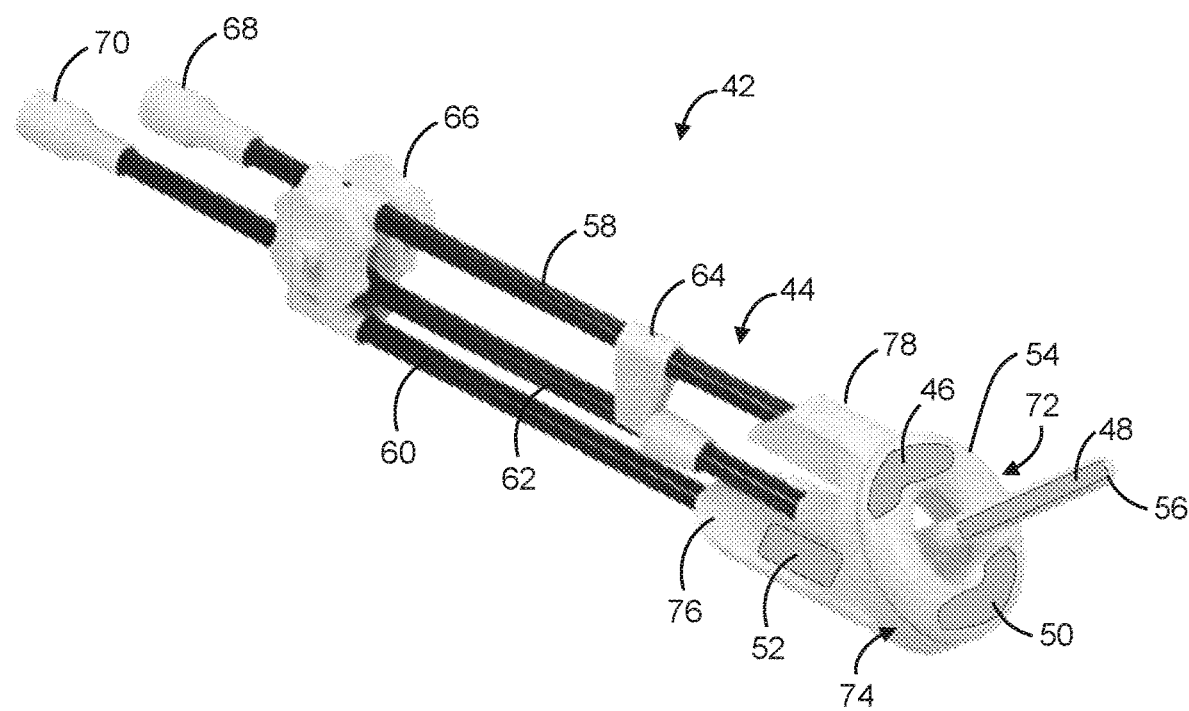
FIG. 3 illustrates another brachytherapy applicator having one or more ultrasound probes located thereon, consistent with embodiments of the present disclosure.

FIG. 3 illustrates another embodiment of a brachytherapy system 42 including a brachytherapy applicator 44 and US sensors 46, 48, 50, and 52. In this embodiment, the brachytherapy applicator 44 is a ring-shaped applicator suitable for volume-based intracavitary cervical brachytherapy. To that end, the brachytherapy applicator 44 includes an ovoid ring 54 and an intrauterine tube 56 extending through ovoid ring 54. A plurality of applicator tubes 58, 62 and the rectal retractor 60 are secured via clamps 64 and 66 and terminate in ports 68 and 70. Each of these components may include the features described above for the applicator tubes 22 and 24, clamp 38, and ports 32 and 34, respectively.

In this embodiment, the US element 48 is disposed along the length of the intrauterine tube 56. The US element 48 in this implementation may take on a variety of sizes, shapes, forms, and arrangements on the intrauterine tube 56. For example, in this or other embodiments described herein, the US element 48 may include an array of probes disposed about the circumference or central axis of the intrauterine tube 56 at one or more locations along the length of the intrauterine tube 56. In other embodiments, the US element 48 may be disposed on a single side of the intrauterine tube 56 (e.g., as shown in FIG. 3), or two elements or element arrays may be disposed on opposite sides of the intrauterine tube 56. Further, in some embodiments, the US element(s) 48 may be positioned on a section of the circumference of the intrauterine tube, ring, rectal retractor, or ovoid tube.

The US elements 46 and 50 in the illustrated embodiment are disposed on a surface 72 of the ovoid ring 54 on opposite sides of the intrauterine tube 56. However, other uniform or non-uniform patterns of US element or element arrays may be disposed in any desired location on the surface 72. Further, in some embodiments, it may be desirable to position the US elements 46 and/or 50 on another portion of the ovoid ring 54, such as on a side portion 74. Indeed, the US probes 46 and/or 50 may be disposed in any desired location on the ovoid ring 54 in other embodiments.

In the illustrated embodiment, the US element or element arrays 52 is positioned on rectal retractor 76 extending from the ovoid ring 54. However, in other embodiments, the US element or element arrays 52 may be positioned in or on another location extending from the ovoid ring 54, such as on extension 78.

Figure 4:
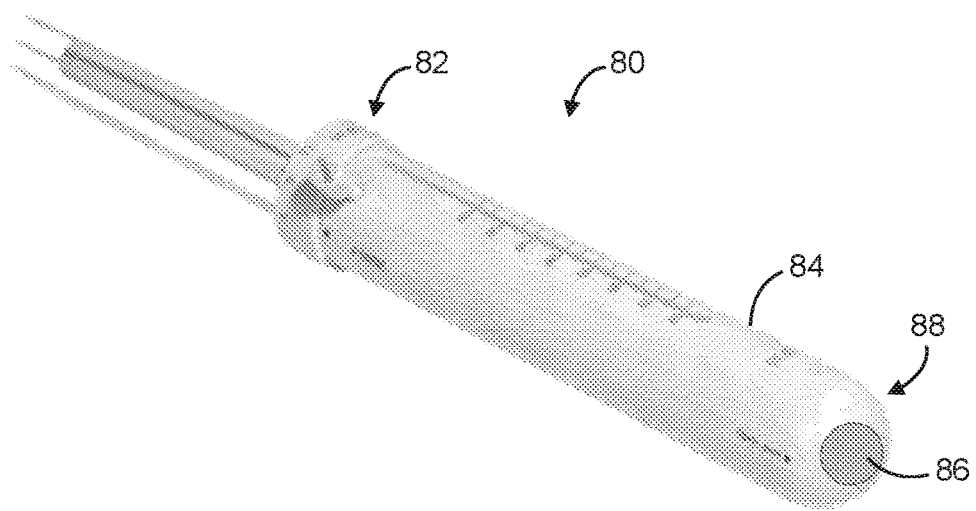
FIG. 4 illustrates another brachytherapy applicator having one or more ultrasound elements located thereon, consistent with embodiments of the present disclosure.

FIG. 4 illustrates another embodiment of a brachytherapy system 80 including a brachytherapy applicator 82 having a body 84 and an US element or element array 86. In this embodiment, the brachytherapy applicator 82 is a vaginal multi-channel applicator. As such, the applicator 82 may incorporate channels that follow the curve of the applicator tip to bring the dosimetry closer to the vaginal vault during operation, thus enabling effective coverage of the planning target volume.

In this implementation, the US element 86 is disposed at a tip 88 of the body 84 of the brachytherapy applicator 82. However, in other embodiments, the US element 86 may be disposed at other locations on the body, or multiple US elements 86 may be provided along the length or about the circumference of the body 84.

Figure 5:
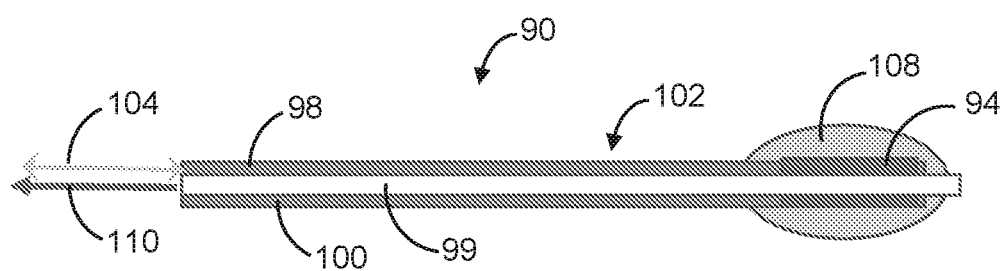
FIG. 5 illustrates a brachytherapy applicator having an ultrasound probe movable in a channel of the applicator, consistent with embodiments of the present disclosure.
Figure 6:
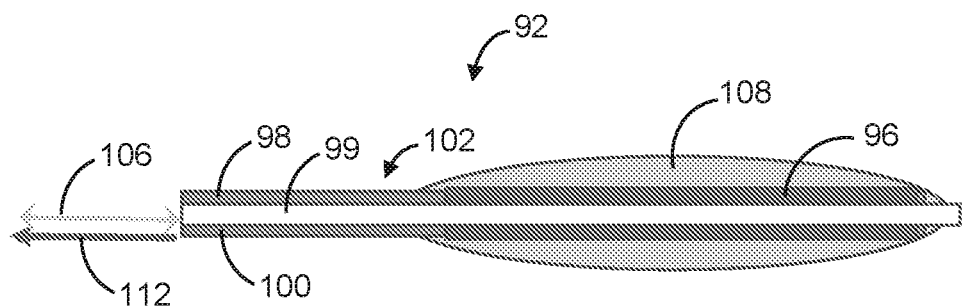
FIG. 6 illustrates another brachytherapy applicator having an ultrasound probe movable in a channel of the applicator, consistent with embodiments of the present disclosure.

FIGS. 5 and 6 are schematics 90 and 92 illustrating additional embodiments in which one or more US probes 94, 96 are inserted in one or more channels of a brachytherapy applicator 102, as indicated by arrows 104 and 106. In these embodiments, an US transmission mechanism 108 is disposed about the one or more US probes or elements 94, 96 to enable transmission of the ultrasonic waves between the US probes 94, 96 and a patient's anatomy. Additionally, one or more conductors (e.g., conducting or optical wires) may be run through the central channel 99, as indicated by arrow 110, and/or one of the other channels 98 and 100, as indicated by arrow 112, to provide power and/or communication between a power and/or control system and the US probes 94 and 96. The power and/or communication may be transmitted electrically, optically, and/or wirelessly in some embodiments.

In some embodiments, the US probes 94 and 96 may be configured to move or slide through one or more of the channels 98, 99, and 100 before, during, and/or after the applicator 102 is positioned within the patient. For example, in one embodiment, the US probes 94 and 96 may be configured to slide along one or more of the channels 98, 99, and 100 and acquire an ultrasonic image at a plurality of locations along the length of the applicator 102. In this embodiment, there may be apertures or windows disposed in the body of the applicator to enable the US probes or elements 94 and 96 to, for example, contact the patient's tissue at a variety of locations. For further example, in certain embodiments, by moving the US probes or elements 94 and 96 within one or more of the channels 98, 99, and 100 and acquiring measurements at multiple positions, a 3D image of the patient's anatomy may be reconstructed. The US probes 94 and 96 may thus enable visualization of the environment within the patient (e.g., with a penetration depth of the acoustic signals being at least approximately 1 mm).

The US probes 94 and 96 may take on a variety of forms in presently contemplated embodiments. For example, in one embodiment, the US probes 94 and 96 may each include a phased array in which multiple US emitting and receiving elements, such as crystals are arranged around the circumference of the applicator 102 in the axial direction. In this embodiment, one or more multiplexers may be provided to limit the quantity or size of the conductors coupling the US probes 94 and 96 to one or more external power and/or control systems.

The US probes 94 and 96 in this embodiment may further include ultrasound emitting and receiving elements like piezoelectric crystals conductively connected with a substrate with conductive tracks like a polyimide flex circuit having conductive tracks (e.g., golden or copper) tracks. In one embodiment, piezoelectric crystal elements may be fixated to a polyimide sheet having conductive tracks. The fixation is such that the piezoelectric crystal elements are conductively connected to the tracks. The piezoelectric crystal may be sliced in segments after connection to the polyimide sheet. At specific positions, multiplexers may be conductively fixated. Also, conductive wires may be conductively attached to the tracks. The signal transmission towards the outside world can also be achieved in an optical way or via wireless transmission. This combination may then be attached to the desired brachytherapy applicator.

In some embodiments, the attachment may be adhesive, while in other embodiments, the combination may be embedded in a plastic layer in or on the brachytherapy applicator. The conductive wires may be guided through a separate channel or be conductive wires integrated in the tubing wall as reinforcement wire of the tubing. In some embodiments, the polyimide sheet may have an extension strip, which is longer than the applicator and can be embedded in a slot of the applicator.

Additionally, in some embodiments, the US probes 94 and 96 may include a crystal array applied along the central axis of the applicator 102 in a single strip or multiple strips, and the applicator 102 may be rotated between approximately 30 degrees and approximately 360 degrees for imaging.

In another embodiment, the US probe 96 may include a phase array of ultrasound receiving and emitting elements, such as crystals, formed in a long array along the length of the applicator 102. In this embodiment, the dimensions of the phased array may be selected such that the treatment region of interest in the patient is covered by the array by varying the length and/or circumference of the phased array. In some embodiments, the phased array may include small crystals mounted on a flex circuit, which may impart flexibility on the applicator 102, thus enabling the applicator 102 to follow curves in the channels 98 and 100.

Further, in some embodiments, the US probes 94 and 96 may include one or more crystals, such as piezoelectric crystals, configured to change shape when an electric current is applied thereto, thus producing sounds waves that can be used to visualize the anatomy of interest. The crystals may be rotating crystals or stationary crystals associated with a rotating mirror. In one embodiment, a piezoelectric crystal may be connected to a rotation wire, and the rotation wire contains conductive wires. The rotation wire connected to the piezoelectric crystal may be within a housing substantially devoid of air. The wire with the piezoelectric crystal may be located at a distal end of the housing, and the proximal end may be rotated. During operation of this assembly, the piezoelectric crystal may fire sideways sound waves to probe the anatomy of interest. In another embodiment, a stationary piezoelectric crystal may be provided to produce sound waves that are deflected by a rotating mirror under an angle selected for the given application. In another embodiment, the rotating mirror may have a changeable angle.

The US transmission mechanism 108 may also take on various suitable forms in different embodiments, depending on implementation-specific considerations. For example, in one embodiment, the US transmission mechanism 108 may be an inflatable balloon that can be inflated to adapt to the patient's anatomy. In this embodiment, a lumen may be provided, for example, in a wall of the applicator 102, to inflate and deflate the balloon with a suitable fluid, such as gel, particles, water, or another transportable medium. Indeed, the medium used to inflate the balloon may be any deformable material that substantially omits air.

In another embodiment, the US transmission mechanism 108 may be a deformable and/or dry material. The deformable material may be shaped as an oval or any other suitable shape for the given application. Further, the deformable material may be sized such that its outer diameter is slightly larger than the inner diameter of the applicator channel such that when a force is applied, the deformable material takes the form of the channel and forces air away from the US probes 94 and 96. Additionally, in some embodiments, the deformable material may be filled with a medium like gel, water, or another suitable fluid. For example, the deformable material may be formed from closed cell foam and may have a water-based material inside the closed cells.

Figure 7:
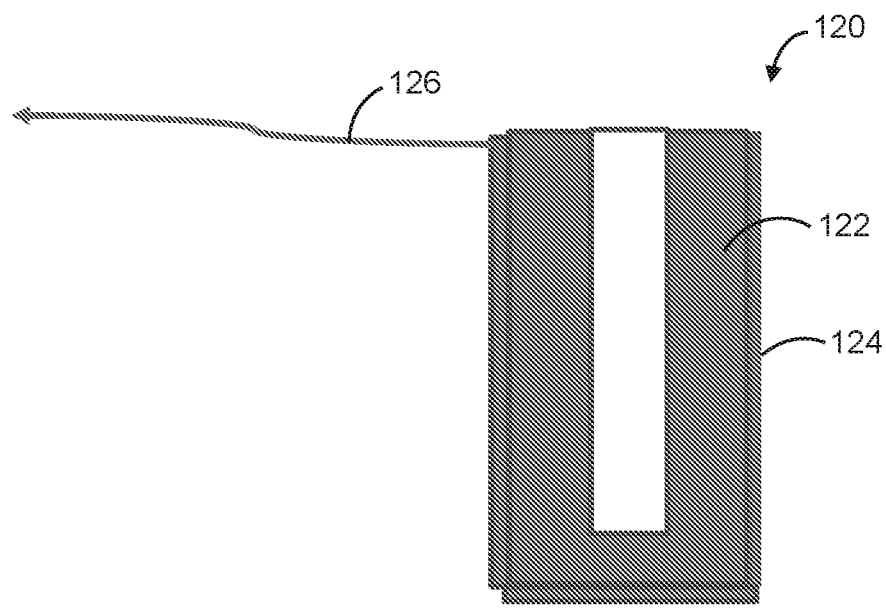
FIG. 7 illustrates an ultrasound element integrated with a brachytherapy applicator, consistent with embodiments of the present disclosure.

FIG. 7 illustrates an embodiment of a brachytherapy applicator 120 including a body 122, which may be a portion of an ovoid or ovoid tubing, having an US probe 124 integrated with an outer surface thereof. A conductor 126 extends from the US probe 124 to couple the US probe 124 to one or more power and/or control systems.

Figure 8:
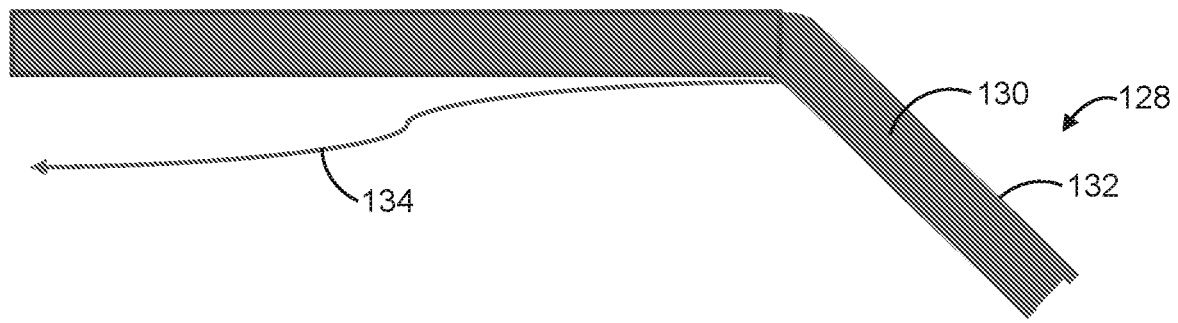
FIG. 8 illustrates another ultrasound element integrated with a brachytherapy applicator, consistent with embodiments of the present disclosure.

Similarly, FIG. 8 illustrates an embodiment of a brachytherapy applicator 128 including a body 130, which may be a portion of an intrauterine tube, having an US element or element array 132 integrated with a portion of an outer surface of an end portion of the body 130. A conductor 134 extends from the US element or element array 132 to couple the US element or element array 132 to one or more power and/or control systems.

In the embodiments of FIGS. 7 and 8, the US element or element array 124 and 132 may be formed as a polyimide layer with tracks, piezoelectric crystals arranged in a phased array, and multiplexers, all covered with an insulative material. The insulative material may be any material suitable for insulating the components of the US probes 124 and 132, such as but not limited to plastic like epoxy.

Further, in embodiments such as those shown in FIGS. 7 and 8 in which the US element or element array 124 and 132 are positioned in or on an outer surface of the applicators 120 and 128, it may be desirable to surround the applicators 120 and 128 with a medium that reduces or prevents the likelihood that air will be present in the vagina. For example, it may be desirable to reduce or prevent the formation of air bubbles because such bubbles may block visualization of the area behind the bubbles. Therefore, in some embodiments, the vagina may be filled by packing with fabric soaked in a gel, filling with a compressible foam or other material, filling with gel, or filling with a compliant balloon full of a material substantially free of air or other undesirable gases.

Figure 9:
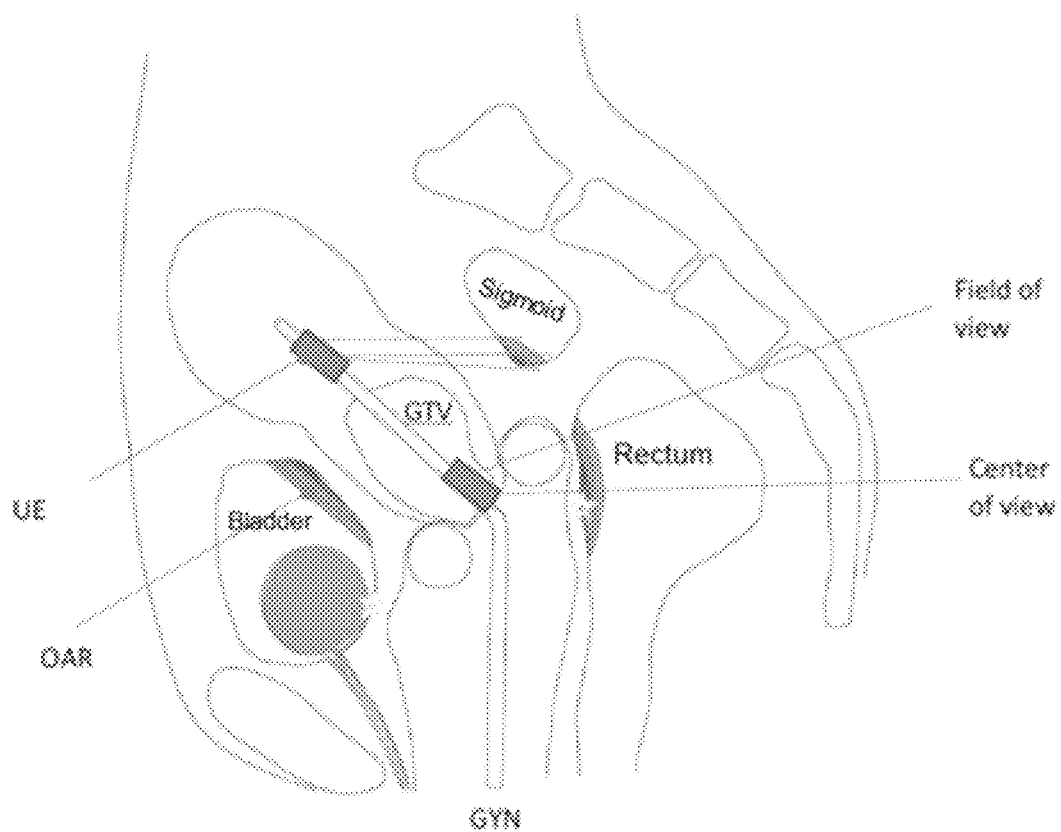
FIG. 9 illustrates another ultrasound element integrated with a brachytherapy applicator, consistent with embodiments of the present disclosure.

FIG. 9 gives a specific embodiment for a gynealogical applicator, wherein the ultrasound element UE is attached to the applicator in order to have a center focus aimed at an organ of interest. Thus the field of view of the ultrasound emitting element is set to a have a direction of view aimed at an organ of interest. This ensures that the organs of interest can be specifically viewed at from a fixed viewpoint, seen from the applicator, which substantially enhances the possibility to control the radiation dose for these organs. In the figure, the volume of an organ at risk (OAR) that gets the highest dose (D2 cc) resulting the dose planning made for treating the tumor can thus be visualized. In more detail imaging requirements for an ultrasound probe in terms of field of view could be for example one or more Ultrasound elements attached to the GYN applicator constructed to carry out one or more of the following steps:

Image the cervix
Image at least ⅔ of the uterus
Image the top of the vagina
Image the D2 cc of the bladder
Image the D2 cc of the rectum
Image the D2 cc of the sigmoid The imaging requirement for an ultrasound probe in terms of resolution would be about 1-5 mm in every direction. For lengths of the uterus typical 8 cm from cervix to fundus and tumors can extend up to 4-5 cm from the cervix in radial direction relative to the GYN applicator.

Similar considerations apply for the embodiment illustrated in FIG. 2. For example, to optimally capture the relevant parts of the cervix the ultrasound elements may be positioned on ovoids 18, 20 on the frontal side "looking forward" and on the free side of the ovoid over at least 90 degrees relative to the axial forward direction, but preferably over 135 degrees. Similarly, US elements can be positioned, in the figure of the drawing, on top, bottom and rear walls of the ovoids 26, 28.

This may be provided by array elements additional to forward looking elements 18, 20 (not shown),that may be placed on the top end bottom surface which may include the transition surface between the top side (or bottom side) and frontal side, top side (or bottom side) and side ovoid top side.

In this way the field view of the combined ultrasound elements of may cover designated area's of interest while the applicator can be designed conformal to the anatomy of the patient.

In FIG. 3, ultrasound elements 46 and/or 50 are preferably positioned covering ring 54 on the frontal side "looking forward" to image the cervix. In addition, ultrasound elements can be positioned on the free sides. The bottom part of the ring is constructed so that a section of the US elements may look backward creating a field of view with an angle of more than 100 degrees, preferably about 135 degrees. This can be provided by a suitable curvature of the ring's bottom face. For schematic reasons ultrasound element 52 is illustrated visibly but is arranged at the side, in use, opposed to the rectum.

In FIG. 4, preferably ultrasound elements 86 are preferably positioned on a circumference of the cylinder and on the distal sphere to image a forward and partly radial direction, seen from the length axis of the cylinder. A distal length of the cylinder 84 that may be covered by the US elements could be between 3 m and 10 cm to cover all area's of interest.

In practical examples, ultrasound frequency to be used to cover 10 cm-15 cm field depth and having an acceptable resolution are preferably between 2.5 MHz and 10 MHz.

As described above, applicators consistent with the above embodiments may be used for brachytherapy treatment. For example, an applicator as shown above in FIGS. 2-4 having one or more US elements may be inserted together into a patient's anatomical cavity, such as the patient's vagina. Additionally or alternatively, and consistent with other disclosed embodiments, such as those shown in FIGS. 5 and 6 above, the applicator may first be inserted and positioned in the patient, and then the US probe may be inserted into the applicator.

Either before or during applicator insertion, in order to optimize ultrasonic visualization, it may be desirable to position one or more of the US elements or US probes in an environment within the patient having a reduced or eliminated amount of gas and/or air. To that end, the environment in the area to be imaged (e.g., the distal 5 cm of the vagina) may be filled with a fluid or solid material either before, during, or after insertion of the applicator.

As described above, a variety of suitable materials could be used to remove the gas or air. Such materials include, but are not limited to, a water-based foam that expands between the applicator and the patient's tissue, a rigid gel compressed between the applicator and the tissue, compliable balloon(s) filled with a material such as saline, a fabric filled with a gel that may be pressed out of the fabric to form a uniform water-based matrix during packaging, a deformable sponge filled with a gel that is compressed in the free space, a water-based foam such as PUR foam, or a two-component composite material that hardens (e.g., within about a minute). Additionally, in one embodiment, the vagina may be filled with a plurality of water-filled particles, thus packing the applicator in place. The particles may be formed from a rubber material having the air removed therefrom, resulting in a rigid, water-filled anatomical shaped system.

Once the applicator, the US elements or probe, and the transmission medium are positioned within the patient's anatomy, the US elements or probe may be activated to transmit acoustic signals into the patient's anatomy through the transmission medium. The acoustic signals interact with the patient's anatomy and one or more devices positioned within the patient, and the US elements or probe then receive acoustic signals that have interacted with the patient's anatomy and the surrounding environment.

In some embodiments in which an US probe is utilized (e.g., as shown in FIGS. 5 and 6), the US probe may be moved over a desired length or portion of the patient's anatomy to obtain a 3D image of the region of interest. The US transmitting and receiving elements in the US probe may also be excited in a specific order to create an ultrasound wave that is able to cover the region of interest at a plurality of positions.

In some embodiments, the data acquired via operation of the US element or probe may be transmitted (e.g., optically, electrically, or wirelessly) to an externally located controller for utilization in planning treatment of the patient. For example, the acquired data may be used in a feedback loop during treatment of the patient to determine the relative position between the tumor, the applicator, and/or one or more other portions of the patient's anatomy. Based on this feedback, the treatment plan and/or the position of the applicator may be modified to improve accuracy and/or effectiveness of treatment of the tumor.

In this disclosure, various embodiments have been described with reference to the accompanying drawings and embodiments. It will, however, be evident that various modifications and changes may be made thereto, and additional embodiments may be implemented, without departing from the present disclosure. The specification and drawings are accordingly to be regarded in an illustrative rather than restrictive sense.

For example, advantageous results may still be achieved if steps of the disclosed methods were performed in a different order and/or if components in the disclosed systems were combined in a different manner and/or replaced or supplemented by other components. Other implementations are also within the scope of the present disclosure.

By way of examples, the following aspects may be identified of the brachytherapy system as herein disclosed. It may comprise a brachytherapy applicator comprising an applicator tube and a radiation source configured to deliver radiation to a tumor, wherein at least a portion of the applicator tube is configured to conform to at least a portion of a patient's anatomy; and at least one ultrasound element, element array, or probe coupled to the applicator tube;

It may comprises a gynecological applicator having at least one ovoid, and the at least one ultrasound element may be coupled to the at least one ovoid; The at least one ovoid may be ring shaped;

The ring shaped ovoid may comprise an intrauterine tube extending therefrom.

The at least one ultrasound element may be disposed on the intrauterine tube.

The brachytherapy applicator may comprise a cylindrical shaped applicator having at least one channel and having the at least one ultrasound element or element array disposed at a distal end of the applicator.

The at least one ultrasound probe or element may comprise a phased array with a multiplexer, a rotating crystal a stationary crystal with a rotating mirror, or a combination thereof.

The system may comprise a brachytherapy applicator comprising a body having at least one channel extending therethrough and being configured to deliver radiation to a tumor; and at least one ultrasound probe configured to be inserted into the at least one channel and moved along the length of the channel.

The at least one ultrasound probe may be configured to acquire an ultrasonic image at more than one location along the length of the at least one channel.

The body of the brachytherapy applicator may comprise a plurality of apertures disposed along the length of the body and configured to align with the at least one ultrasound probe.

The brachytherapy system may comprise an electrical or optical conductor coupled to the at least one ultrasound probe and configured to be received in the at least one channel.

The brachytherapy system may comprise an ultrasound transmission medium disposed between the at least one ultrasound probe and the vaginal tumor or anatomy.

The transmission medium may comprise gel, water, foam, powder, or a combination thereof.

The at least one ultrasound probe may comprise a piezoelectric crystal, a multiplexer, a polyimide flex circuit, or a combination thereof.

The at least one ultrasound probe comprises a rotating crystal or a stationary crystal and a rotating mirror.

The brachytherapy system may comprise a brachytherapy applicator comprising an applicator tube and at least one ovoid coupled to the applicator tube and configured to conform to at least a portion of a patient's vagina; and at least one ultrasound element or element array disposed on an outer surface of or integrated in a wall of the brachytherapy applicator.

The at least one ultrasound probe may comprises a polyimide layer, one or more piezoelectric crystals, and a multiplexer.

The the polyimide layer, the one or more piezoelectric crystals, and the multiplexer may be covered with a layer of insulative material.

The insulative material may comprises plastics, thermoplastics, or thermos-hardeners.

The outer surface may be a surface shaped to the patients anatomy, in particular, be of the at least one ovoid.

The brachytherapy applicator may further comprise ovoid tubing, and the outer surface is a surface of the ovoid tubing.

The brachytherapy applicator may further comprise an intrauterine tube, and the outer surface is a surface of the intrauterine tube.

It is to be understood that both the foregoing general description are exemplary and explanatory only, and are not restrictive. Further, the accompanying drawings, which are incorporated in and constitute a part of this specification, illustrate embodiments of the present disclosure and together with the description, and are similarly not restrictive.

The invention claimed is:

1. A brachytherapy system, comprising:
    a brachytherapy applicator comprising an applicator body having an applicator tube and a radiation source configured to deliver radiation to a tumor, wherein the radiation source is received within the applicator tube, and wherein at least a portion of the applicator body is configured to conform to at least a portion of a patient's anatomy; and
    at least one ultrasound element, ultrasound element array, or ultrasound probe disposed on or within the applicator tube, wherein the at least one ultrasound element, ultrasound element array, or ultrasound probe is configured to produce or receive ultrasound signals.

2. The brachytherapy system of claim 1, wherein at least a portion of the applicator tube is configured to conform to the at least a portion of a patient's anatomy.

3. The brachytherapy system of claim 1, wherein the brachytherapy applicator comprises a gynecological applicator, wherein the applicator tube includes at least one ovoid, and wherein the at least one ultrasound element, ultrasound element array, or ultrasound probe is disposed on the at least one ovoid.

4. The brachytherapy system of claim 3, wherein the at least one ovoid is ring shaped.

5. The brachytherapy system of claim 4, wherein the ring shaped ovoid comprises an intrauterine tube extending therefrom.

6. The brachytherapy system of claim 5, wherein the at least one ultrasound element, ultrasound element array, or ultrasound probe is disposed on the intrauterine tube.

7. The brachytherapy system of claim 1, wherein the applicator tube has at least one channel, and the at least one ultrasound element, ultrasound element array, or ultrasound probe is disposed at a distal end of the applicator tube.

8. The brachytherapy system of claim 1, wherein the at least one ultrasound element, ultrasound element array, or ultrasound probe comprises one or more of a phased array with a multiplexer, a rotating crystal, or a stationary crystal with a rotating mirror.

9. The brachytherapy system of claim 1, wherein the applicator tube has at least one channel extending therethrough, and wherein the least one ultrasound element, ultrasound element array, or ultrasound probe is dimensioned to be moved along a length of the at least one channel.

10. The brachytherapy system of claim 9, comprising an electrical or optical conductor coupled to the at least one ultrasound element, ultrasound element array, or ultrasound probe and configured to be received in the at least one channel.

11. The brachytherapy system of claim 1, wherein the body of the brachytherapy applicator comprises a plurality of apertures disposed along a length of the body.

12. The brachytherapy system of claim 1, comprising an ultrasound transmission medium disposed adjacent the at least one ultrasound element, ultrasound element array, or ultrasound probe and configured to be positioned between the at least one ultrasound element, ultrasound element array, or ultrasound probe and a tumor when the brachytherapy system is in use.

13. The brachytherapy system of claim 12, wherein the transmission medium comprises at least one of gel, water, foam, or powder.

14. The brachytherapy system of claim 1, wherein the at least one ultrasound element, ultrasound element array, or ultrasound probe comprises at least one of a piezoelectric crystal, a multiplexer, or a polyimide flex circuit.

15. The brachytherapy system of claim 1, wherein the applicator tube includes at least one ovoid, wherein the applicator tube is configured to conform to at least a portion of a patient's vagina, and wherein the at least one ultrasound element, ultrasound element array, or ultrasound probe is disposed on an outer surface of or is integrated in a wall of the applicator tube.

16. The brachytherapy system of claim 15, wherein the outer surface is a surface of the at least one ovoid.

17. The brachytherapy system of claim 15, wherein the applicator tube further comprises ovoid tubing, and the outer surface is a surface of the ovoid tubing.

18. The brachytherapy system of claim 15, wherein the applicator tube further comprises an intrauterine tube, and the outer surface is a surface of the intrauterine tube.

19. The brachytherapy system of claim 1, wherein the at least one ultrasound element, ultrasound element array, or ultrasound probe comprises a polyimide layer, one or more piezoelectric crystals, and a multiplexer.

20. The brachytherapy system of claim 19, wherein the polyimide layer, the one or more piezoelectric crystals, and the multiplexer are covered with a layer of insulative material.

21. The brachytherapy system of claim 20, wherein the insulative material comprises at least one of a plastic, thermoplastic, or thermo-hardener.

22. A brachytherapy system, comprising:
a gynecological brachytherapy applicator comprising an applicator body and a radiation source configured to deliver radiation to a tumor, wherein at least a portion of the applicator body is configured to conform to at least a portion of a patient's anatomy, and wherein the applicator body includes at least one ring-shaped ovoid having an intrauterine tube extending therefrom; and
at least one ultrasound element, ultrasound element array, or ultrasound probe coupled to the applicator body coupled to the at least one ovoid.

23. A brachytherapy system, comprising:
a brachytherapy applicator comprising an applicator body and a radiation source configured to deliver radiation to a tumor, wherein at least a portion of the applicator body is configured to conform to at least a portion of a patient's anatomy, wherein the applicator body has at least one channel extending therethrough, and wherein the applicator body comprises a plurality of apertures disposed along a length of the body; and
at least one ultrasound element, ultrasound element array, or ultrasound probe coupled to the applicator body, wherein the least one ultrasound element, ultrasound element array, or ultrasound probe is dimensioned to be inserted into the at least one channel and moved along a length of the at least one channel, and wherein the at least one ultrasound element, ultrasound element array, or ultrasound probe is configured to acquire a first ultrasonic image at a first location and a second ultrasonic image at a second location along the length of the at least one channel.

* * * * *